(12) United States Patent
Manzo

(10) Patent No.: US 7,349,857 B2
(45) Date of Patent: Mar. 25, 2008

(54) PROCESS FOR FORMULATING A CUSTOMIZED SKIN CARE PRODUCT

(76) Inventor: Robert P. Manzo, 16 Spruce Hill La., Goshen, NY (US) 10924

( * ) Notice: Subject to any disclaimer, the term of this patent is extended or adjusted under 35 U.S.C. 154(b) by 229 days.

(21) Appl. No.: 10/409,843

(22) Filed: Apr. 9, 2003

(65) Prior Publication Data

US 2004/0202685 A1 Oct. 14, 2004

(51) Int. Cl.
*G06Q 10/00* (2006.01)
*C12Q 1/00* (2006.01)

(52) U.S. Cl. ............................................... 705/2; 435/4
(58) Field of Classification Search .................... 705/1, 705/2, 3, 7, 26, 27, 400, 500; 435/4; 600/300; 702/19; 424/401
See application file for complete search history.

(56) References Cited

U.S. PATENT DOCUMENTS

| | | | |
|---|---|---|---|
| 5,789,191 A * | 8/1998 | Mayer et al. .................. 435/39 |
| 6,068,848 A * | 5/2000 | Gubernick et al. .......... 424/401 |
| 6,121,243 A * | 9/2000 | Lanzendorfer et al. ....... 514/28 |
| 6,358,539 B1 * | 3/2002 | Murad ......................... 424/725 |
| 6,596,761 B2 * | 7/2003 | Lanzendorfer et al. ..... 514/456 |
| 6,673,756 B2 * | 1/2004 | Sonnenberg et al. ........ 510/141 |
| 6,923,975 B2 * | 8/2005 | Aronson et al. ............. 424/401 |
| 2003/0014324 A1 * | 1/2003 | Donovan et al. .............. 705/26 |
| 2003/0064350 A1 * | 4/2003 | Rubinstenn et al. .......... 434/99 |
| 2003/0065552 A1 * | 4/2003 | Rubinstenn et al. .......... 705/10 |
| 2003/0093297 A1 * | 5/2003 | Schilling et al. ................ 705/2 |
| 2003/0211068 A1 * | 11/2003 | O'Prey et al. ............ 424/70.14 |
| 2004/0081674 A1 * | 4/2004 | Franke ........................ 424/401 |
| 2004/0126604 A1 * | 7/2004 | Wang et al. ................. 428/500 |
| 2004/0236592 A1 * | 11/2004 | Aleles et al. ................... 705/1 |

FOREIGN PATENT DOCUMENTS

WO WO01/18674 A2 * 3/2001

* cited by examiner

*Primary Examiner*—Igor N. Borissov
(74) *Attorney, Agent, or Firm*—Evelyn A. Defilló; Defillo & Associates, Inc

(57) ABSTRACT

The invention relates to a method and a process of determining individual skin structure and function at a point in time for the purpose of determining and formulating skin care products that remedy the deficiencies observed in the skin. Objective and repeatable dermal biometric instrumentation techniques can be used to measure skin moisture content, sebum content, firmness and elasticity properties, skin thickness, transepidermal water loss, skin pH and to perform a photo analysis of the face with UV and visible light. By customizing the skin care products, the individually added active ingredients can be controlled, the diluents can be modified, dermal penetration rates can be controlled, the surfactant systems can be adjusted, and the stability of the product can be controlled. To prevent the loss of active materials in the product, the skin care product is manufactured for an individual consumer and is only sold in a quantity of a three months supply. Additionally, a variety of ingredients can be combined that a mass produced product cannot contain due to stability/compatibility issues. This invention overcomes the limitations in formulating skin products for the mass market by providing a product designed with objective biometric data and created for the specific clinical condition of an individual's skin.

1 Claim, No Drawings

PROCESS FOR FORMULATING A CUSTOMIZED SKIN CARE PRODUCT

FIELD OF THE INVENTION

The invention concerns a process for determining individual skin structure and function at a point in time for the purpose of determining and formulating skin care products.

BACKGROUND OF THE INVENTION

Skin care product development has been an evolving science for hundreds of years. Soaps were one of the first cleansing products to be manufactured. With the evolution of synthetic detergents (surfactants) in the 1940's and 1950's, additional opportunities arose in product formulation by combining oil soluble materials with water soluble materials. Through much of the 20th century, skin care preparations were primarily moisturizers and emollients. From the 1970's through today, technology has advanced the development of active ingredients to enhance the skin's appearance. These materials include alpha and beta hydroxy acids, retinol derivatives, vitamin derivatives, advanced bio-engineered ingredients which stimulate collagen and elastin syntheses, ingredients which suppress protein enzyme activity, natural moisturizing factors and even human fibroblast conditioned media. The technology continues to become more sophisticated as it evolves both within major manufacturers of skin care products as well as within the suppliers who develop base ingredients for these manufacturers.

Dermal biometrics (sometimes called bioengineering techniques) have significantly improved over the last decade. Measurement of skin properties and function became critical in supporting representations for products placed in the mass retail trade. Representations like "improves fine lines and wrinkles", "improves skin firmness by x %", etc. are commonplace in the market today. These representations are made through the analysis of large groups of panelist volunteers who allow themselves to be measured using biometric techniques along with experimental skin care products. The types of skin properties that are tested include moisturization, firmness, elasticity, sebum amount, skin thickness, skin profilometry, trans-epidermal water loss (barrier function), and photographic analysis (visible and UV to determine photo damage).

Several problems arise when formulating skin care products for the mass market. One problem involves formulating a product to accommodate the largest possible group with any product claim that is made. This explains the proliferation of skin "type" products in the market. Types include: oily, dry, combination, acne prone, sun sensitive, sensitive skin, allergy tested, poor texture, large pores, etc. The manufacturers must strike a balance between what is economically feasible for them relative to the quantity of products available in the market and the amount of customers they can attract from the market.

A second problem that formulators face is product stability. Most responsible manufactures formulate for a 1-3 year shelf life which means that current formulations must contain surfactants, stabilizers, preservatives, and other ingredients in their products. These stabilizing ingredients degrade actives such as retinol, vitamin C and many others. The stabilizers can also affect the penetration parameters of the active ingredients. It is not at all uncommon to analyze formulas from the shelf and find that the retinol or vitamin C values have deteriorated to a zero percent concentration. Bio-engineering specialty ingredients can also be sensitive to heat and light. Unfortunately, however, these products are exposed to temperature fluctuations ranging between freezing and 140° F. or more during manufacturing and distribution. This makes formulating with the active ingredients very difficult. By the time that the product gets to the market, there may be a significant reduction in the concentration of active materials remaining in the products.

One company, Reflect.com, has attempted to solve these problems by creating "customized" products for consumers. Their website notes that mass-produced products follow trends and fall into generic categories, but that the mass-produced products do not take the consumer's specific, individual needs into consideration. The website touts a revolutionary customization process that meets each person's individual beauty needs and desires with "a precision that has never been available before."

However, the problem with Reflect.com's approach to customized skin-care is that subjective data is used to produce their customized products. The products are created using only data compiled from answers to inquiries. This subjective data is further compromised by the fact that the consumers answer the questions themselves, further skewing the answers from reality by their own perceptions and misconceptions.

Another company, Lab 21, takes an approach similar to Reflect.com. They use a "21" question questionnaire in order to obtain data. Then, they use the results of the questionnaire to design customized skincare formulations. The problem with the Lab 21 approach is the same as the problem with Reflect.com; they use subjective data in order to create their customized products.

Previously, the technological biometric instrumentation required to collect an individual's objective skin profile was not available to the mass market. Such instruments were bulky and expensive. Due to recent developments in the field of dermal biometric evaluation, however, hand-held sized instruments which are more sophisticated and easier to use are now available and being sold at an affordable price.

Currently, only major skin care manufacturers, dermatologists, cosmetic surgeons and other medical and skin care professionals are using these state of the art instruments. For example, Proctor and Gamble have launched a program using their VISIA technology. This photographic imaging tool provides clinical measurement and analysis of topical and subsurface facial skin conditions. Medical and skincare professionals in the fields of dermatology and cosmetic surgery have used the digital skin imaging and quantitative image analysis as a breakthrough tool that allows them to be more effective communicators and to better track medical treatment outcomes by analyzing and scoring skin features.

The challenge faced by the use of the VISIA system is that it is only an imaging technique and gives no objective data relative to the mechanical aspects of skin structure and function such as moisturization, elasticity, etc.

SUMMARY OF THE INVENTION

The task of the present invention is thus to use objective, repeatable biometric instrumentation techniques to measure an individual's skin structure and function and to produce customized skin care products which have precisely targeted ingredients to remedy skin deficiencies identified in the clinical biometric analysis. By customizing the skin care products, the individually added active ingredients can selected to target specifically identified needs and can be added at precise doses, the diluents can be modified, dermal penetration rates can be controlled, the surfactant systems can be adjusted, and the stability of the product can be controlled. Therefore, by combining new state-of-the-art dermal biometric techniques with skin care product development, products can now be produced that have a clear performance benefit compared to others in the market specifically tailored to the individual consumer.

Objective biometric instrumentation techniques can be used to measure skin moisture content, sebum content, firmness and elasticity properties, skin thickness, trans-epidermal water loss, and to perform a photo analysis of the face with UV and visible light. An example of possible, but not limiting, instrumentation techniques can be found listed in the following table:

| Technique | Dermal Property Measured |
|---|---|
| Trans-epidermal water loss | Barrier function |
| Corneometry | Skin Moisture |
| Chromametry | Skin Color |
| Cutometry | Skin Elasticity & Firmness |
| Sebumetry | Skin sebum |
| Sonography | Skin thickness |
| Profilometry | Skin roughness |
| Laser-Doppler flowmetry | Blood flow |
| Visible Imaging | Wrinkles, texture, pore size |
| Ultra-Violet Imaging | Photo-damage, oil balance, bacteria |
| Skin pH | Relative acid-alkaline property of skin |

There are many more bioengineering techniques available as well. By using any combination of these techniques, one can characterize aspects of the subject's skin structure and function at a point in time. These techniques can be used to evaluate a subject's skin in a smaller, less clinical and more comfortable environment in less time. Another advantage is that all of these techniques are non-invasive and therefore safe for both the subject and the analyst.

The data obtained from the biometric instrumentation techniques provide a very good understanding of the current condition of an individual's skin structure and function at that point in time. This combination of data will be referred to herein as a Skinprint™. The Skinprint™ is sent to a formulating laboratory where the parameters of the Skinprint™ are interpreted. The formulating chemist then adds the correct ingredients at the precise dosages in order to confer the maximum benefits to the skin where it is needed. Finally, the formulator prepares approximately a three months supply of the product(s) for the consumer to use.

This invention overcomes the limitations in formulating skin products for the mass market by providing a product designed with objective biometric data and created for the specific clinical condition of an individual's skin. To prevent the loss of active materials in the product, the skin care product is manufactured for an individual consumer and is only sold in a quantity of a three months supply. Additionally, a variety of a combination of ingredients can be used that a mass produced product cannot combine due to stability/compatibility issues in order to produce a dramatically more effective product.

An additional benefit is conferred by this customized objective method. The improvement of the skin can be tracked by measuring the same person using the same techniques on a regular basis. Thus, the formulations can be modified as needs arise for dose changes, ingredients requirements, seasonal, climate, age and "adaptation" issues.

While "individual" is used throughout this specification, it also to be understood that any process described herein can also apply to a small group of individuals. Accordingly, this specification should not be construed as limiting the invention to data obtained from a single individual and customizing a skin product for a single individual. A small group of individuals could be measured in order to customize a product for an individual. Further, a small group of individuals could be measured in order to customize a product for a small group of individuals. Likewise, an individual could be measured in order to customize a product for a small group of individuals. For example, this process could be applied to identical twins, twins, siblings, family members, members of the same geographical region of the same age group, etc. If members of the same genetic composition, the same age, sun exposure, humidity levels, ultraviolet levels, etc. are sampled, it is entirely possible to take the data obtained from one, or several, person(s) and customize a skin care product for one, or several, person(s) in that same group.

DETAILED DESCRIPTION OF THE INVENTION

Example 1

A subject visits either a spa environment or a specialty skin care boutique to obtain specialty custom blended skin care products. Inside the spa/boutique, the subject is greeted by a certified The Skin Atelier™ (TSA) analyst. Next, the subject is escorted to a climate recorded room. Inside the room, the subject engages in an evaluation with the TSA consultant and fills out a specific lifestyle questionnaire.

The questionnaire elicits information on age, sex, ethnicity, current skin care usage, past skin care usage, the subject's perception of their skin, known allergies, reactions of any kind, formulation preferences relative to product aesthetics, water intake habits, smoking habits, relevant medical history, diet, and the subject's perception of their: skin type, moisture content, oil level and texture. The subject completes the questionnaire for two reasons: to gather relevant information about the subject and to acclimate the subject's skin to a specific, known temperature and humidity contained in the room, so as to allow for repeatable measurements in future assessments. This process takes approximately 20-30 minutes.

Next, the client changes into an appropriate garment for the assessment. The skin area to be analyzed undergoes a specific preparation protocol. Either a mild washing procedure or other preparation is undertaken to standardize the preparation procedure for future assessments. The following procedures can be performed on any part of the subject's skin. For ease of explanation, the following example will focus on the subject's face. However, this discussion should not be construed as limiting the invention.

The following techniques are preferred primarily due to the fact that the results of the analyses are actionable from a topical skin care delivery system.

The client is placed in a reclining chair/chaise and placed in a standardized, semi-prone comfortable position. The semi-prone position is utilized so that the subject's skin can be measured in the same position each time the test is done. The same position should be used to avoid negatively affecting skin taughtness, which could create an inaccurate elasticity/firmness analysis, as well as negatively impacting other testing techniques and values.

The Skinprint™ bioengineering unit can be calibrated by the analyst before the subject arrives. Then, the analyst will digitally photograph the subject's face in the standardized position with a visible and then a UV light source. The visible imaging measures overall appearance, wrinkles, texture and pore size. The UV imaging measures photo-damage, oil balance and bacterial presence. The subject's photographs can appear on the monitor and also can be captured on the hard drive of the computer. The imaging is done by digital high-resolution photography with a visible light source and a UV light source. The images are sent directly to the computer. Additionally, each of the measurements taken throughout the testing process is automatically recorded into the computer.

Next, the analyst sets the instrument in the moisturization mode. The probe is placed on approximately five fixed positions on the face, but the number of fixed positions may vary depending upon the circumstances. The computer automatically records the moisture level of those positions. The data is recorded in Seiman units, which is a measure of electrical conductance. The higher the water content of the skin, the higher the electrical conductance.

Then, the analyst sets the instrument to calculate the next measurement, which is a barrier function test. Then, the analyst places the probe on four fixed positions on the face. The trans-epidermal water loss (TEWL) is measured until a steady state is reached for the measurement in each of the four fixed positions, which occurs in approximately two minutes per position. The TEWL is measured as the analyst watches a real time measurement of the TEWL of the measured area to ensure the steady state. The data is measured in $mg/cm^2$. This test is a measure of the moisture coming off the skin as measured between two transducers of a fixed distance within one probe. The more disrupted the barrier function of the skin, the more moisture comes off the skin.

The analyst sets the instrument to perform the next test, which is elasticity and firmness. The analyst places a suction cup probe on four fixed positions on the face where the analyst observes a dynamic real time graph. Elasticity and firmness are measured by alternately applying negative pressure to the skin and relaxing the negative pressure. This process takes approximately thirty seconds to one minute per position. This method measures both skin elongation and repeatability. The subject experiences a slight "sucking" feeling on the skin. The more force required by the vacuum, measured in kilopascals (kPa), to "suck" the skin, the tighter the skin is and the higher the number will be. The tightness of the skin has a direct correlation to the skin elasticity and function.

The last test performed measures the sebum content of the skin. The analyst applies a new strip of Sebutape™ to each of seven fixed positions on the face by hand. Each strip of tape is pressed firmly on each position, held for about five seconds and removed. The tape is placed into a transducer that computes the surface area of darkened tape and provides that number to the computer. The amount of darkened verses light tape is a direct correlation to the amount of sebum being produced in that position of the subject's face. The sebum values are measured in arbitrary units (au), which is obtained from the amount of tape that was darkened by sebum.

The analyst concludes the Skinprint™ program by exporting the data to the database and image database. The subject's Skinprint™ is complete. The face, or any other part of the body which was analyzed, is cleaned. The subject is given a copy of the data from a computer readout. Then, the analyst engages in a consultation with the subject to discuss the results of and conclusions drawn from the data.

At least five possible customized products can be created from the objective data obtained from this procedure: cleanser, exfoliator, serums, treatment cream and daily moisturizer. A full range of custom blended products can be developed to the subject's liking as well.

The Skinprint™ is given to the formulating laboratory for interpretation of the data obtained from the individual subject as a result of the instrumental and imaging techniques. At the formulating laboratory, an analysis of the characteristics of the subject's skin takes place. These include skin moisture, barrier function, elasticity, firmness, sebum, wrinkles, texture, pore size, bacterial presence, pH and photo-damage. Decisions are made with respect to active ingredients, base ingredients, and the number of individual products needed. Examples of decisions made with respect to this interpretation include but are not limited to:

Moisture: occlusive, humectant, natural moisturizing ingredients or others as appropriate.

Barrier function: occlusive agents, anti-irritants, natural moisturizing factors (NMF's), lipid stimulating ingredients Elasticity: elastase inhibitors, collagen/elastin synthesis promoters Firmness: collagenase inhibitors, collagen synthesis promoters, polymers, vitamins and their derivatives Sebum: 5 alpha reductase inhibitors to control, skin emollients for absence Photo-damage: sunscreens, DNA repair enzymes, antioxidants Wrinkles: collagen promoters, moisturizers, alpha hydroxyl acids, retinol Texture: alpha hydroxyl acids, retinol Bacteria: anti-bacterials, bacteriostats These are only a select group of possible ingredients that can be used to remedy undesired skin performance. The total palette of ingredients is vast and is covered in relevant literature. Trade Journals, such as the *International Federation of the Society of Cosmetic Chemists,* and texts, such as the *Handbook of Cosmetic Science and Technology* (2001), the International Cosmetic Ingredient Dictionary and Handbook ($_8$th ed.), and the Cosmetic Bench Reference are incorporated herein by reference.

There are several important factors that the formulators consider when custom blending formulations such as in the present invention. The consideration of these factors provides an advantage over other products of the same type. These include but are not limited to:

1. Dosage: With the skin structure and function known, the formulator can apply the precise dosage of active and inert ingredients to maximize the effectiveness of the formula.

2. Active selection: The formulation, based on the Skinprint™ and a questionnaire, provides the formulator with the ability to correctly formulate the proper ingredients to avoid known irritancy issues, allergy issues, adaptation effects and others.

3. Control delivery: The formulator has the ability to formulate the active ingredients in a base which will have the optimal dermal penetration, topical spreading ability, low irritancy or whatever issue is defined by the Skinprint™ and questionnaire.

4. Freshness of sensitive ingredients: It is well know that many effective active ingredients are highly perishable in delivery systems. Vitamin C and retinol are two such ingredients that survive for only a short period of time in standard formulations. This invention allows the subjects to receive the products within days of manufacture.

5. Repeat Skinprints: Each subject is recommended to receive at least four assessments per year. This allows the formulator to track the effectiveness of the formulas by comparing the clinical assessments between time periods. The formulator will adjust formulas, bases and product forms to achieve a long term positive result which can be objectively measured by the methods described herein.

6. Preservative reductions: Due to the minimal amount of shelf storage time and exposure to light and heat that the formulations experience, preservatives are reduced. By reducing the amount of preservatives, the potential for irritation of the subject is limited.

By combining state-of-the-art bioengineering techniques with the ability to formulate custom blended products for individual clients, product performance is optimized.

Example 2

Subject A 25 year old, female, Caucasian, no known allergies, no previous reactions to skin care products, non-smoker, drinks 2 glasses of water a day, does not use a daily sunscreen, 5'7", 140#, endures occasional skin acne outbreaks.

| Technique | Measurement |
| --- | --- |
| Visible Imaging | Identified initiation of fine lines/wrinkles around eyes and mouth, occasional blemishes, overall good tone and texture |
| Ultra-Violet Imaging | Identified moderate photo damage evenly dispersed throughout the facial skin surface. |
| Corneometry | Measured 24/32/35/28 (siemens) forehead/l.cheek/r.cheek/chin |
| TEWL | Measured 15/22/20/17 (mg/sq.cm.) forehead/l.cheek/r.cheek/chin |
| Cutometry | Measured 35./38/45.4 l.cheek/r.cheek/forehead |
| Sebemetry | Measured 23/20/28/24 (arbitrary units) l.cheek/r.cheek/forehead/chin |

Ingredients Added/Rationale:
1. Indications of excess sebum were present: added glycyrrhiza extract (Lichochalcone LR-15) at a dosage of 0.05-0.1% to regulate sebum flow and inhibit the growth of P.acnes in a moisturizing and penetrating base.
2. Indications of moderate photo damage were present. added a blend of plankton extract in liposomal (Photosomes®) form at 1%, retinol at 0.05-0.1%, an antioxidant blend such as Scavenol™ at 0.2-0.5%, all in a serum hydrogel base with no surfactants present.
3. Recommended a sunscreen maintenance moisturizer with a minimum SPF of 15, glycyrrhiza extract and active humectants.

Subject B 55 year old, female, caucasian, currently uses moisturizer and daily sunscreen, no known allergies, no previous reactions to skin care products, smoker, exhibits hyperpigmentation on face, drinks 4 glasses of water a day, diet is normal, 5'3", 120#, has somewhat dry skin

| Technique | Measurement |
| --- | --- |
| Visible Imaging | Identified hyperpigmentation on random areas of face, moderate lines and wrinkles around eyes and mouth, skin texture exhibited an "orange peel" look. |
| Ultra-Violet Imaging | Identified low-moderate photo damage |
| Corneometry | Measured 18/22/21/25 seimens forehead/l.cheek/r.cheek/chin |
| TEWL | Measured 32/35/49/29 Forehead/l.cheel/r.cheek/chin |
| Cutometry | Measured 18/21/33 l.cheek/r.cheek./chin |
| Sebemetry | Measured 11/15/16/12 l.cheel/r.cheek/forehead/chin |

Ingredients Added/Rationale
1. Some photo damage was present in combination with smoking and barrier function impairment: added stabilized vitamin C tetrahexyldecyl ascorbate (BV-OSC) 0.5-1.0%, ursolic acid in liposomal form (merospheres) 1%, Scavenol™ at 0.5-1.0% in a serum base.
2. Significant reduction in skin firmness and elasticity was present: added palmitoyl-pentapeptide 3 (Matrixyl®) at 50 ppm active, hydrolyzed lupin protein at 1.0%, clycine soja extract (isoflavone SG-10) in a penetrating serum base.
3. Low sebum and corneometry results: added active humectants, occlusive agents such as dimethicone in a moisturizing base with SPF 15 minimum.

The words used in this specification to describe the present invention are to be understood not only in the sense of their commonly defined meanings, but to include by special definition, structure, material, or acts beyond the scope of the commonly defined meanings. The definitions of the words or elements of the following claims are, therefore, defined in this specification to include not only the combination of elements which are literally set forth, but all equivalent structure, material, or acts for performing substantially the same function in substantially the same way to obtain substantially the same result.

In addition to the equivalents of the claimed elements, obvious substitutions now or later known to one of ordinary skill in the art are defined to be within the scope of the defined elements.

The claims are thus to be understood to include what is specifically illustrated and described above, what is conceptually equivalent, what can be obviously substituted, and also what incorporates the essential idea of the invention.

I claim:

1. A process for determining a specific individual skin structure and formulating a skin care product based only on the specific individual skin structure, the process consisting of:
   a) placing the specific individual into a room having a known temperature and humidity, wherein the temperature and humidity are recorded at the time the individual is placed into the room;
   b) measuring at least one biometric skin parameter on the skin of the specific individual by instrumental and imaging techniques;
   c) generating a data set based only on the specific individual skin structure measurement;

d) selecting ingredients for the specific individual skin structure based only on the data set interpretation of the results of step c); and
e) formulating the skin care product with the selected ingredients of step d), wherein the skin care product is custom made only for the specific individual based on the specific individual skin structure at the time of the measurement.

* * * * *